(12) United States Patent
Cox et al.

(10) Patent No.: US 7,723,365 B2
(45) Date of Patent: May 25, 2010

(54) MITOTIC KINESIN INHIBITORS

(75) Inventors: Christopher D. Cox, Harleysville, PA (US); Mark E. Fraley, North Wales, PA (US); Robert M. Garbaccio, Landsdale, PA (US)

(73) Assignees: Merck & Co., Inc., Rahway, NJ (US); Merck Sharp & Dohme Corp., Rahway, NJ (US)

( * ) Notice: Subject to any disclaimer, the term of this patent is extended or adjusted under 35 U.S.C. 154(b) by 542 days.

(21) Appl. No.: 11/660,288

(22) PCT Filed: Aug. 15, 2005

(86) PCT No.: PCT/US2005/028990

§ 371 (c)(1),
(2), (4) Date: Feb. 15, 2007

(87) PCT Pub. No.: WO2006/031348

PCT Pub. Date: Mar. 23, 2006

(65) Prior Publication Data

US 2008/0153887 A1 Jun. 26, 2008

Related U.S. Application Data

(60) Provisional application No. 60/602,481, filed on Aug. 18, 2004.

(51) Int. Cl.
*A61K 31/4245* (2006.01)
*C07D 271/10* (2006.01)

(52) U.S. Cl. .................. 514/364; 548/125; 548/143; 514/361

(58) Field of Classification Search ............... 548/125, 548/143; 514/361, 364
See application file for complete search history.

(56) References Cited

U.S. PATENT DOCUMENTS

| | | | | | |
|---|---|---|---|---|---|
| 3,509,169 | A | * | 4/1970 | Marsh | 548/143 |
| 6,566,311 | B1 | * | 5/2003 | Nalesnik | 508/278 |
| 7,449,486 | B2 | * | 11/2008 | Hans et al. | 514/363 |
| 7,504,413 | B2 | * | 3/2009 | Qian et al. | 514/300 |

FOREIGN PATENT DOCUMENTS

WO   WO 03/079973   10/2003

OTHER PUBLICATIONS

Geller, Hanno (1945): STN International HCAPLUS database, (Columbus, Ohio), Accession No. 1945:7982.*
Nalesnik, Theodore E. (2003): STN International HCAPLUS database, (Columbus, Ohio), Accession No. 2003:390834.*
Yandovskii et al (1978): STN International HCAPLUS database, (Columbus, Ohio), Accession No. 1978:443520.*
Somogyi, L, Carbohydrate Research, vol. 182, pp. 19-29 (1988), "Stereochemical aspects of the formation of diastereoisomeric 3-acetyl-2-polyacetoxyalkyl)-5-phenyl-2,3-dihydro-1,3,4-oxadiazoles".
Somogyi, L, Tetrahedron, vol. 41, No. 22, pp. 5187-5190 (1985), "Notes on the reactions of ketone acylhydrazones under acylation conditions".
Szczepankiewicz, BG et al., J. Med. Chem., vol. 44, pp. 4416-4430 (2001), "New antimitotic agents with activity in multi-drug-resistant cell lines and in vivo efficacy in murine tumor models".

* cited by examiner

*Primary Examiner*—Golam M Shameem
(74) *Attorney, Agent, or Firm*—Nicole M. Beeler; David A. Muthard

(57) ABSTRACT

The present invention relates to oxadiazoles that are useful for treating cellular proliferative diseases, for treating disorders associated with KSP kinesin activity, and for inhibiting KSP kinesin. The invention also relates to compositions which comprise these compounds, and methods of using them to treat cancer in mammals.

3 Claims, No Drawings

MITOTIC KINESIN INHIBITORS

PRIORITY CLAIM

This application is a 371 application of PCT/US2005/028990 that was filed on Aug. 15, 2004, which claims priority from the U.S. Provisional Application No. 60/602,481, filed on Aug. 18, 2004, now expired.

BACKGROUND OF THE INVENTION

This invention relates to oxadiazoles that are inhibitors of mitotic kinesins (in particular the mitotic kinesin KSP) and are useful in the treatment of cellular proliferative diseases, for example cancer, hyperplasias, restenosis, cardiac hypertrophy, immune disorders and inflammation.

Among the therapeutic agents used to treat cancer are the taxanes and vinca alkaloids. Taxanes and vinca alkaloids act on microtubules, which are present in a variety of cellular structures. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force that drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins that have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997); Blangy, et al., Cell Motil Cytoskeleton, 40:174-82 (1998); Whitehead and Rattner, J. Cell Sci., 111: 2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol. Endocrinol., 9:243-54 (1995); GenBank accession number L40372]. Xenopus KSP homologs (Eg5), as well as Drosophila K-LP61 F/KRP 130 have been reported.

Mitotic kinesins are attractive targets for the discovery and development of novel mitotic chemotherapeutics. Accordingly, it is an object of the present invention to provide compounds, methods and compositions useful in the inhibition of KSP, a mitotic kinesin.

SUMMARY OF THE INVENTION

The present invention relates to oxadiazoles that are useful for treating cellular proliferative diseases, for treating disorders associated with KSP kinesin activity, and for inhibiting KSP kinesin.

DETAILED DESCRIPTION OF THE INVENTION

The compounds of this invention are useful in the inhibition of mitotic kinesins. A first embodiment of the instant invention is a compound as illustrated by Formula I:

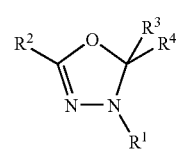

wherein:
a is 0 or 1; b is 0 or 1; m is 0, 1 or 2;
$R^1$, $R^2$, $R^3$ and $R^4$ are independently selected from: H, $CF_3$, $NO_2$, $(C=O)_aO_b(C_1-C_{10})$alkyl, $(C=O)_aO_b(C_2-C_{10})$alkenyl, $(C=O)_aO_b(C_2-C_{10})$alkynyl, $(C=O)_aO_b(C_3-C_8)$cycloalkyl, $(C=O)_aO_b(C_0-C_6)$alkylene-aryl, $(C=O)_aO_b(C_0-C_6)$alkylene-heterocyclyl, $(C=O)_aO_b(C_0-C_6)$alkylene-$N(R^d)_2$, $O_b(C_1-C_3)$perfluoroalkyl, $(C_0-C_6)$alkylene-$S(O)_mR^a$, $(C_0-C_6)$alkylene-$CO_2R^aC(O)H$, $(C_0-C_6)$alkylene-$CO_2H$, and $S(O)_mN(R^b)_2$; said alkyl, alkenyl, alkynyl, cycloalkyl, aryl, alkylene and heterocyclyl are optionally substituted with up to three substituents selected from $R^7$;

$R^7$ is independently selected from: H, halogen, $CF_3$, $(C_1-C_6)$alkyl, $(C=O)_aO_b(C_1-C_6)$alkyl, $(C=O)$cycloalkyl, $(C=O)$aryl, $(C=O)$heterocyclyl, $(C_3-C_8)$cycloalkyl, aryl, heterocyclyl, OH, oxo, CN, $(C_1-C_6)$alkyl-OH, $(C_1-C_6)$alkyl-$N(R^c)_2$ $N(R^c)_2$, $-OP(O)OH_2$ and $-O(C=O)(C_1-C_6)$alkyl;

$R^a$ is selected from: $(C_1-C_6)$alkyl, $(C_3-C_8)$cycloalkyl, aryl and heterocyclyl; said alkyl, cycloalkyl, aryl and heterocyclyl is optionally substituted with one or more substituents selected from $R^7$;

$R^b$ is independently selected from: H, $(C_1\text{-}C_6)$alkyl and heterocyclyl;

$R^c$ is independently selected from: H and $(C_1\text{-}C_6)$alkyl;

$R^d$ is independently selected from: H, $O_a(C_1\text{-}C_6)$alkyl, $(C_1\text{-}C_6)$alkyl-heterocyclyl, $(C_3\text{-}C_8)$cycloalkyl, aryl and heterocyclyl, said alkyl, cycloalkyl, aryl and heterocyclyl optionally substituted with up to three substituents selected from $R^7$;

or a pharmaceutically acceptable salt or stereoisomer thereof.

A second embodiment of the instant invention is a compound as illustrated by Formula I:

wherein:

$R^1$ is selected from: H, $CF_3$, $NO_2$, $(C=O)_aO_b(C_1\text{-}C_{10})$alkyl, $(C=O)_aO_b(C_2\text{-}C_{10})$alkenyl, $(C=O)_aO_b(C_2\text{-}C_{10})$alkynyl, $(C=O)_aO_b(C_3\text{-}C_8)$cycloalkyl, $(C=O)_aO_b(C_0\text{-}C_6)$alkylene-aryl, $(C=O)_aO_b(C_0\text{-}C_6)$alkylene-heterocyclyl, $(C=O)_aO_b(C_0\text{-}C_6)$alkylene-N$(R^d)_2$, $O_b(C_1\text{-}C_3)$perfluoroalkyl, $(C_0\text{-}C_6)$alkylene-S(O)$_m R^a$, $(C_0\text{-}C_6)$alkylene-CO$_2R^a$, C(O)H, $(C_0\text{-}C_6)$alkylene-CO$_2$H, and S(O)$_m$N$(R^b)_2$; said alkyl, alkenyl, alkynyl, cycloalkyl, aryl, alkylene and heterocyclyl is optionally substituted with up to three substituents selected from $R^7$;

$R^2$ is selected from: $(C_3\text{-}C_8)$cycloalkyl, aryl and heterocyclyl; said cycloalkyl, aryl and heterocyclyl optionally substituted with up to three substituents selected from $R^7$;

$R^3$ is selected from: H, $(C_1\text{-}C_6)$alkyl-N$(R^d)_2$, $(C_1\text{-}C_6)$alkyl-heterocyclyl, $(C_1\text{-}C_6)$alkyl-OH, $O_b(C_1\text{-}C_{10})$alkyl, $(C_3\text{-}C_8)$cycloalkyl, aryl, heterocyclyl, N$(R^d)_2$, $(C_1\text{-}C_6)$alkyl(O)$(C_1\text{-}C_6)$alkyl, said alkyl, cycloalkyl, aryl and heterocyclyl optionally substituted with up to three substituents selected from $R^8$;

$R^4$ is selected from: $(C_3\text{-}C_9)$cycloalkyl, aryl and heterocyclyl; said cycloalkyl, aryl and heterocyclyl optionally substituted with up to three substituents selected from $R^7$;

$R^8$ is independently selected from: H, halogen, $(C_1\text{-}C_6)$alkyl, $(C=O)_aO_b(C_1\text{-}C_6)$alkyl, $(C=O)$cycloalkyl, $(C=O)$aryl, $(C=O)$heterocyclyl, $(C_3\text{-}C_8)$cycloalkyl, aryl, heterocyclyl, OH, oxo, CN, $(C_1\text{-}C_6)$alkyl hydroxyl, N$(R^c)_2$, —OP(O)OH$_2$ and —O(C=O)$(C_1\text{-}C_6)$alkyl;

$R^d$ is independently selected from: H, $O_a(C_1\text{-}C_6)$alkyl, $(C_1\text{-}C_6)$alkyl-heterocyclyl, $(C_3\text{-}C_8)$cycloalkyl and heterocyclyl, said alkyl, cycloalkyl and heterocyclyl optionally substituted with up to three substituents selected from $R^7$;

and all other substituents and variables are as defined in the first embodiment;

or a pharmaceutically acceptable salt or stereoisomer thereof

A third embodiment of the instant invention is a compound as illustrated by Formula II:

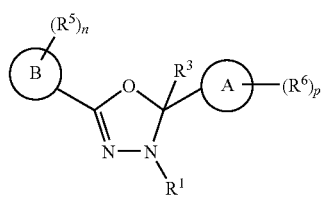

wherein:

n and p are independently 0, 1, 2, 3, 4 or 5;

A and B are independently selected from: $(C_3\text{-}C_8)$cycloalkyl, aryl and heterocyclyl;

$R^3$ is selected from: H, $(C_1\text{-}C_6)$alkyl-N$(R^d)_2$, $(C_1\text{-}C_6)$alkyl-heterocyclyl, $(C_1\text{-}C_6)$alkyl-OH, $O_b(C_1\text{-}C_{10})$alkyl, $(C_3\text{-}C_8)$cycloalkyl, heterocyclyl, N$(R^d)_2$, $(C_1\text{-}C_6)$alkyl(O)$(C_1\text{-}C_6)$alkyl, said heterocyclyl optionally substituted with up to three substituents selected from $R^8$;

$R^5$ is independently selected from: H, $CF_3$, $(C_1\text{-}C_6)$alkyl, $(C_1\text{-}C_6)$alkyl-N$(R^c)_2$, N$(R^c)_2$, halogen and OH;

$R^6$ is independently selected from: H, $(C_1\text{-}C_6)$alkyl, halogen and OH;

and all other substituents and variables are as defined in the second embodiment;

or a pharmaceutically acceptable salt or stereoisomer thereof.

A fourth embodiment of the instant invention is a compound as illustrated by Formula III:

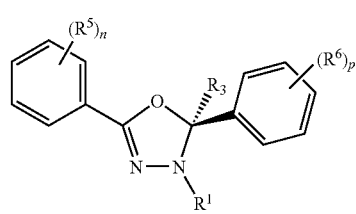

wherein:

all other substituents and variables are as defined in the third embodiment;

or a pharmaceutically acceptable salt or stereoisomer thereof.

Specific examples of the compounds of the instant invention include:

3-acetyl-5-(2,5-difluorophenyl)-2-phenyl-2,3-dihydro-1,3,4-oxadiazole (1-3);

3-acetyl-5-(2,5-difluorophenyl)-2-methyl-2-phenyl-2,3-dihydro-1,3,4-oxadiazole (2-2);

3-[3-acetyl-5-(2,5-difluorophenyl)-2-phenyl-2,3-dihydro-1,3,4-oxadiazol-2-yl]propan-1-ol (3-5); and 3-[3-acetyl-5-(2,5-difluorophenyl)-2-phenyl-2,3-dihydro-1,3,4-oxadiazol-2-yl]-N,N-dimethylpropan-1-amine (3-6);

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

When any variable (e.g. $R^5$ and $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkylene" means a hydrocarbon diradical group having the specified number of carbon atoms. For example, "alkylene" includes —$CH_2$—, —$CH_2CH_2$— and the like.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, —$CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, diazepanyl, diazepanonyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

In an embodiment, A is ($C_3$-$C_9$)cycloalkyl, aryl or heterocyclyl.

In another embodiment A is phenyl.

In an embodiment, B is ($C_3$-$C_8$)cycloalkyl, aryl or heterocyclyl.

In another embodiment B is phenyl.

In an embodiment, n is 1, 2 or 3.

In another embodiment, n is 1 or 2.

In another embodiment, n is 2.

In an embodiment, p is 0, 1, 2 or 3.

In another embodiment, p is 0, 1 or 2.

In another embodiment, p is 0.

In an embodiment, $R^1$ is selected from: H, $CF_3$, $NO_2$, $(C=O)_aO_b(C_1$-$C_{10})$alkyl, $(C=O)_aO_b(C_2$-$C_{10})$alkenyl, $(C=O)_aO_b(C_2$-$C_{10})$alkynyl, $(C=O)_aO_b(C_3$-$C_8)$cycloalkyl, $(C=O)_aO_b(C_0$-$C_6)$alkylene-aryl, $(C=O)_aO_b(C_0$-$C_6)$alkylene-heterocyclyl, $(C=O)_aO_b(C_0$-$C_6)$alkylene-N($R^d$)$_2$, $O_b(C_1$-$C_3)$perfluoroalkyl, $(C_0$-$C_6)$alkylene-S(O)$_mR^a$, $(C_0$-$C_6)$alkylene-$CO_2R^a$, C(O)H, $(C_0$-$C_6)$alkylene-$CO_2H$, and $S(O)_mN(R^b)_2$; said alkyl, alkenyl, alkynyl, cycloalkyl, aryl, alkylene and heterocyclyl is optionally substituted with up to three substituents selected from $R^7$.

In an embodiment, $R^1$ is selected from: $(C=O)_aO_b(C_1$-$C_6)$alkyl, $(C=O)_aO_b(C_3$-$C_8)$cycloalkyl, aryl and heterocyclyl; said alkyl, cycloalkyl, aryl and heterocyclyl are optionally substituted with 1-3 substituents selected from $R^7$.

In another embodiment, $R^1$ is selected from: $(C=O)_aO_b(C_1$-$C_6)$alkyl-phenyl, $(C=O)_aO_b(C_3$-$C_8)$cycloalkyl and $(C=O)_aO_b(C_1$-$C_6)$alkyl.

In another embodiment, $R^1$ is $(C=O)(C_1$-$C_6)$alkyl.

In an embodiment, $R^2$ is selected from: $(C_3\text{-}C_8)$cycloalkyl, aryl and heterocyclyl; said cycloalkyl, aryl and heterocyclyl optionally substituted with up to three substituents selected from $R^7$.

In another embodiment, $R^2$ is phenyl, optionally substituted with 1-3 substituents selected from halo.

In another embodiment, $R^2$ is:

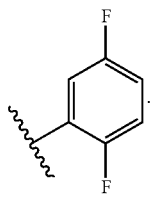

In an embodiment, $R^3$ is selected from: H, $(C_1\text{-}C_6)$alkyl-N$(R^d)_2$, $(C_1\text{-}C_6)$alkyl-heterocyclyl, $(C_1\text{-}C_6)$alkyl-OH, $O_b(C_1\text{-}C_{10})$alkyl, $(C_3\text{-}C_8)$cycloalkyl, heterocyclyl, N$(R^d)_2$, $(C_1\text{-}C_6)$alkyl(O)$(C_1\text{-}C_6)$alkyl, said heterocyclyl optionally substituted with up to three substituents selected from $R^7$.

In another embodiment, $R^3$ is selected from: H, $(C_1\text{-}C_6)$alkyl-N$(R^d)_2$, $(C_1\text{-}C_6)$alkyl-heterocyclyl, $(C_1\text{-}C_6)$alkyl-OH, $O_b(C_1\text{-}C_{10})$alkyl, $(C_3\text{-}C_8)$cycloalkyl, aryl, heterocyclyl, N$(R^d)_2$, $(C_1\text{-}C_6)$alkyl(O)$(C_1\text{-}C_6)$alkyl, said alkyl, cycloalkyl, aryl and heterocyclyl optionally substituted with up to three substituents selected from $R^8$.

In another embodiment, $R^3$ is selected from: H, $(C_1\text{-}C_6)$alkyl-N$(R^d)_2$, $(C_1\text{-}C_6)$alkyl-heterocyclyl, $(C_1\text{-}C_6)$alkyl-OH, $O_b(C_1\text{-}C_{10})$alkyl, $(C_3\text{-}C_8)$cycloalkyl, heterocyclyl, N$(R^d)_2$, $(C_1\text{-}C_6)$alkyl(O)$(C_1\text{-}C_6)$alkyl, said heterocyclyl optionally substituted with up to three substituents selected from $R^8$.

In an embodiment, $R^3$ is selected from: $(C_1\text{-}C_6)$alkyl-N$(R^d)_2$, $(C_1\text{-}C_6)$alkyl-heterocyclyl and $(C_1\text{-}C_6)$alkyl-OH, said heterocyclyl optionally substituted with up to three substituents selected from $R^8$.

In another embodiment, when $R^3$ is $(C_1\text{-}C_6)$alkyl-heterocyclyl, said heterocyclyl is selected from:

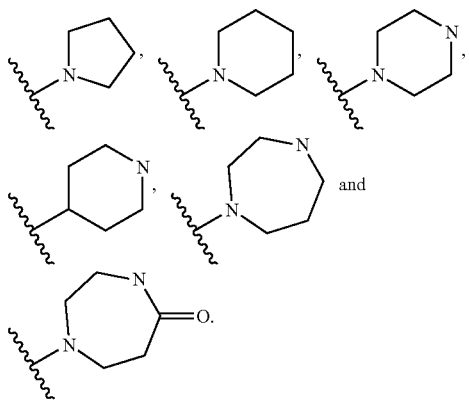

In another embodiment, $R^3$ is selected from: H, $(C_1\text{-}C_6)$alkyl and $(C_1\text{-}C_6)$alkyl-N$(R^d)_2$.

In an embodiment, $R^4$ is selected from: $(C_3\text{-}C_8)$cycloalkyl, aryl and heterocyclyl; said cycloalkyl, aryl and heterocyclyl optionally substituted with up to three substituents selected from $R^7$.

In another embodiment, $R^4$ is phenyl.

In an embodiment, $R^5$ is independently selected from: H, $CF_3$, $(C_1\text{-}C_6)$alkyl, $(C_1\text{-}C_6)$alkyl-N$(R^c)_2$, N$(R^c)_2$, halogen and OH;

In another embodiment, $R^5$ is halogen.

In another embodiment, $R^5$ is F.

In an embodiment, $R^7$ is independently selected from: H, halogen, $CF_3$, $(C_1\text{-}C_6)$alkyl, $(C=O)_aO_b(C_1\text{-}C_6)$alkyl, $(C=O)$cycloalkyl, $(C=O)$aryl, $(C=O)$heterocyclyl, $(C_3\text{-}C_8)$cycloalkyl, aryl, heterocyclyl, OH, oxo, CN, $(C_1\text{-}C_6)$alkyl-OH, $(C_1\text{-}C_6)$alkyl-N$(R^c)_2$, N$(R^c)_2$, $-\text{OP(O)OH}_2$ and $-\text{O(C=O)}(C_1\text{-}C_6)$alkyl.

In another embodiment, $R^7$ is independently selected from: phenyl, halogen, $CF_3$, $(C_1\text{-}C_6)$alkyl$(C_1\text{-}C_6)$alkyl-N$(R^c)_2$ and N$(R^c)_2$.

In an embodiment, $R^8$ is independently selected from: H, halogen, $(C_1\text{-}C_6)$alkyl, $(C=O)_aO_b(C_1\text{-}C_6)$alkyl, $(C=O)$cycloalkyl, $(C=O)$aryl, $(C=O)$heterocyclyl, $(C_3\text{-}C_8)$cycloalkyl, aryl, heterocyclyl, OH, oxo, CN, $(C_1\text{-}C_6)$alkyl hydroxyl, N$(R^c)_2$, $-\text{OP(O)OH}_2$ and $-\text{O(C=O)}(C_1\text{-}C_6)$alkyl.

In another embodiment, $R^8$ is independently selected from: N$(R^c)_2$, $(C_1\text{-}C_6)$alkyl, OH, halogen, oxo and $(C_1\text{-}C_6)$alkyl-OH.

In another embodiment, $R^b$ is independently selected from: H and $(C_1\text{-}C_6)$alkyl.

In an embodiment, $R^d$ is independently selected from: H, $O_a(C_1\text{-}C_6)$alkyl, $(C_1\text{-}C_6)$alkyl-heterocyclyl, $(C_3\text{-}C_8)$cycloalkyl, aryl, and heterocyclyl, said alkyl, cycloalkyl, aryl and heterocyclyl optionally substituted with up to three substituents selected from $R^7$.

In another embodiment, $R^d$ is independently selected from: H, $O_a(C_1\text{-}C_6)$alkyl, $(C_1\text{-}C_6)$alkyl-heterocyclyl, $(C_3\text{-}C_8)$cycloalkyl and heterocyclyl, said alkyl, cycloalkyl and heterocyclyl optionally substituted with up to three substituents selected from $R^7$.

In another embodiment, $R^d$ is independently selected from: H and $(C_1\text{-}C_6)$alkyl.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of Formula I hereinabove.

Reaction Schemes

In one embodiment, substituted benzohydrazides (A-1) can be combined with substituted 1-phenyl alkyl-1-ones (A-2) to provide phenylalkylidenyl benzohydrazides (A-3). By the action of heating in acetic anhydride, cyclization will occur to give 2,3-dihydro-1,3,4-oxadiazoles (A-4).

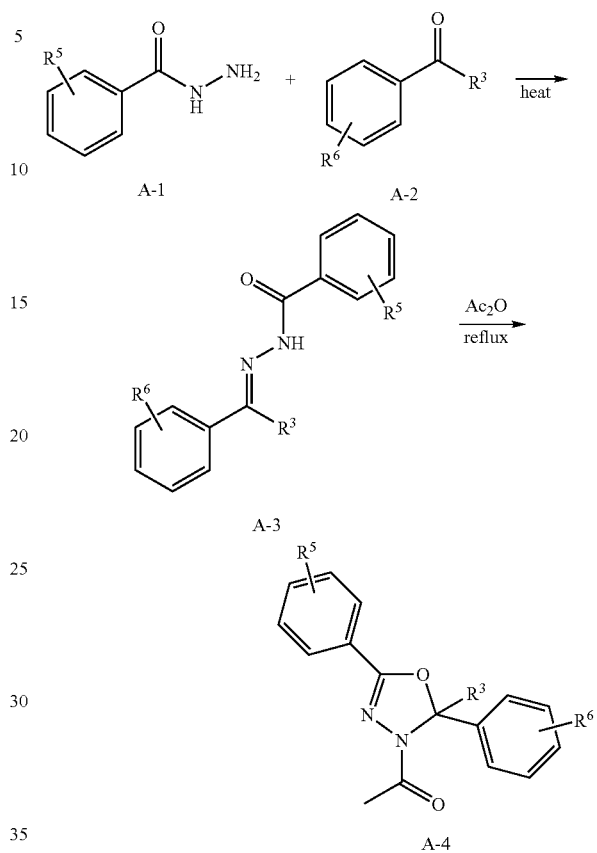

Utility

The compounds of the invention find use in a variety of applications. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In an embodiment, the compounds of the invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to and/or modulate the activity of a mitotic kinesin. In an embodiment, the mitotic kinesin is a member of the bimC subfamily of mitotic kinesins (as described in U.S. Pat. No. 6,284,480, column 5). In a further embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. In addition, other mitotic kinesins may be inhibited by the compounds of the present invention.

The compounds of the invention are used to treat cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals which are afflicted or may eventually become afflicted with any one of these disorders or states.

The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

The compounds of the invention are also useful in preparing a medicament that is useful in treating the cellular proliferation diseases above, in particular cancer.

The compounds of the instant invention may also be useful as antifungal agents, by modulating the activity of the fungal members of the bimC kinesin subgroup, as is described in U.S. Pat. No. 6,284,480.

The compounds of the invention are also useful in preparing a medicament that is useful in treating the diseases described above, in particular cancer.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. For purposes of this application, topical application shall include mouth washes and gargles.

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678 and WO 03/39460 and pending PCT Appl. Nos.

US03/06403 (filed Mar. 4, 2003), US03/15861 (filed May 19, 2003), US03/15810 (filed May 19, 2003), US03/18482 (filed Jun. 12, 2003) and US03/18694 (filed Jun. 12, 2003). In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy 14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see

*Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-ε agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration"

and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist; an inhibitor of cell proliferation and survival signaling, an agent that interfers with a cell cycle checkpoint, an apoptosis inducing agent and a bisphosphonate.

These and other aspects of the invention will be apparent from the teachings contained herein.

Abbreviations used in the description of the chemistry and in the Examples that follow are: 9-BBN (9-borabicyclo[3.3.1] nonane); Ac$_2$O (acetic anhydride), AcOH (acetic acid); DCE (dichloromethane); Dess-Martin Periodinane (1,1,1-tris(aceteloxy)-1,1-benziodoxol-3-(1H)-one); DIBAL-H (diisobutylaluminum hydride); DIEA (diisopropylethylamine); DMAP (4-dimethylaminopyridine); DME (ethylene glycol dimethyl ether); DMF (dimethylformamide); DMSO (dimethyl sulfoxide); DTT (dithiothreitol); EDC (1-(3-dimethylaminopropyl)-3-ethylcarbodiimide hydrochloride); EtOAc (ethyl acetate); FACS (fluorescence activated cell sorting); FITC (Fluorescein isothiocyanate); HOBt (1-hydroxybenzotriazole); IPTG (Isopropyl-beta-D-thiogalactopyranoside); LDA (lithium diisopropylamide); LHMDS (lithium hexamethyldisilazide); mCPBA (m-chloroperoxybenzoic acid); MS (mass spectrometry); NaHMDS (sodium bistrimethylsilylamide); NMR (nuclear magnetic resonance); PMSF (phenylmethylsulphonyl fluoride); PyBop (1H-1,2,3-benzotriazol-1-yloxy)(tripyrrolidin-1-yl)phosphonium hexafluorophosphate); Rochelle's salt (potassium sodium tartrate); SiO$_2$ (silica gel); TBAI (tetra-n-butylammonium iodide); TEA (triethyl amine); THF (tetrahydrofuran); TFA (trifluoroactic acid); TMSCN (trimethylsilylcyanide); TsCl (p-toluenesulfonyl chloride) and Weinreb amide (N-methyl-N-methoxy amide).

EXAMPLES

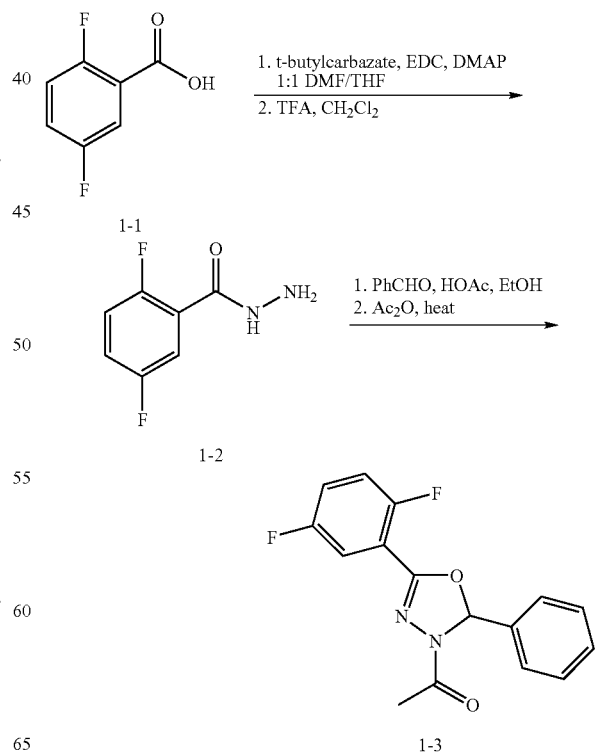

3-acetyl-5-(2,5-difluorophenyl)-2-phenyl-2,3-dihydro-1,3,4-oxadiazole (1-3)

To a solution of 5.0 g (31.6 mmol) of 2,5-difluorobenzoic acid (1-1) in 20 mL of 1:1 THF/DMF was added 4.39 g (33.2 mmol) of t-butylcarbazate, 6.67 g (34.8 mmol) of EDCI, and 50 mg of DMAP. After stirring for 3 h at room temperature, the reaction was dumped into ice water and extracted three times with ether. The combined organic phases were washed two times with 10% citric acid, two times with saturated NaHCO$_3$, once with water, once with brine, and then dried over MgSO$_4$. Concentration by rotary evaporation provided the BOC-protected acyl hydrazine as a white solid. To a solution of 1.5 g (5.5 mmol) of this material in 20 mL of CH$_2$Cl$_2$, cooled to 0° C., was added 10 mL of trifluoroacetic acid, and the resultant mixture was allowed to stir for 2 h at that temperature. The volatiles were removed by rotary evaporation, the residue was partitioned between EtOAc and aqueous NaHCO$_3$, the layers were separated, and the aqueous phase was extracted two more times with EtOAc. The combined organic phases were washed twice with saturated NaHCO$_3$, brine, dried over Na$_2$SO$_4$, and concentrated to provide 663 mg (3.85 mmol) of 2,5-difluorobenzohydrazide (1-2) as a white solid. This material was dissolved in 30 mL of EtOH, and then 1.5 mL of HOAc was added, followed by 390 μL (3.85 mmol) of benzaldehyde. After stirring for 1 h at room temperature, the solvents were removed by rotary evaporation, and the residue was triturated with Et$_2$O to provide the imine as a white powder. A portion of this imine (225 mg, 0.86 mmol) was dissolved in 3 mL of acetic anhydride and heated at 125° C. for 2 h After cooling to room temperature, the volatiles were removed by rotary evaporation, the residue was dissolve in EtOAc, washed twice with saturated NaHCO$_3$, water, dried over Na$_2$SO$_4$, and concentrated. The residue was then purified by column chromatography with a gradient of EtOAc in hexanes to provide (1-3) as a white solid. $^1$H NMR (500 MHz, CDCl$_3$): δ 7.6-7.4 (m, 6H), 7.2 (m, 2H), 7.1 (s, 1H), 2.4 (s, 3H) ppm. HRMS (ES) calc'd M+H for C$_{16}$H$_{12}$F$_2$N$_2$O$_2$: 303.0940; found 303.0926.

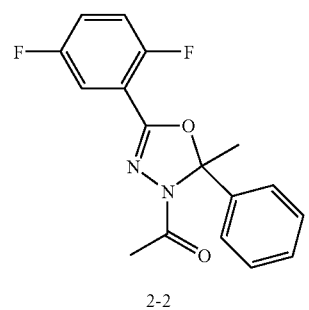

3-acetyl-5-(2,5-difluorophenyl)-2-methyl-2-phenyl-2,3-dihydro-1,3,4-oxadiazole (2-2)

A solution of 2,5-difluorobenzohydrazide (1-2, 90 mg, 0.52 mmol, 1 equiv) and acetophenone (61 μL, 0.52 mmol, 1.0 equiv) was heated in EtOAc (10 mL) at 75° C. for 3 d. The reaction mixture was concentrated to give 2,5-difluoro-N'-[(1E)-1-phenylethylidene]benzohydrazide (2-1); LRMS m/z (M+H) 275.1 found, 275.1 required. A solution of 2-1 in acetic anhydride (5 mL) was heated at reflux for 1.5 h. The reaction mixture was concentrated and the residue was purified by reverse-phase LC (H$_2$O/CH$_3$CN gradient w/0.1% TFA present) to provide 3-acetyl-5-(2,5-difluorophenyl)-2-methyl-2-phenyl-2,3-dihydro-1,3,4-oxadiazole (2-2) as a colorless oil. $^1$H NMR (300 MHz, CDCl$_3$) δ 7.56 (m, 2H), 7.48 (m, 1H), 7.39 (m, 3H), 7.14 (m, 2H), 2.35 (s, 3H), 2.30 (s, 3H). LRMS m/z (M+H) 317.2 found, 317.1 required.

SCHEME 2

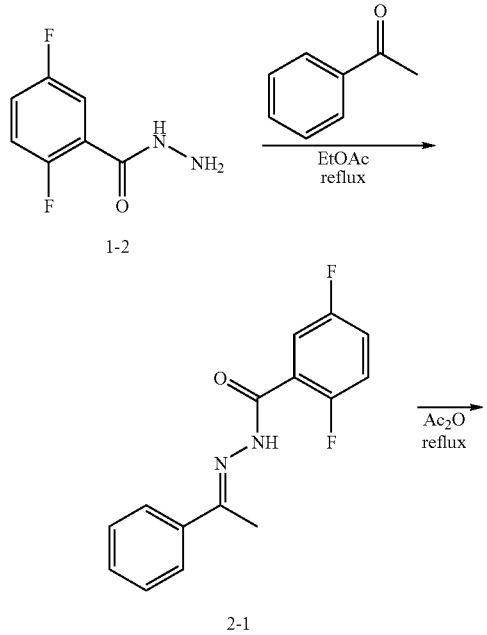

SCHEME 3

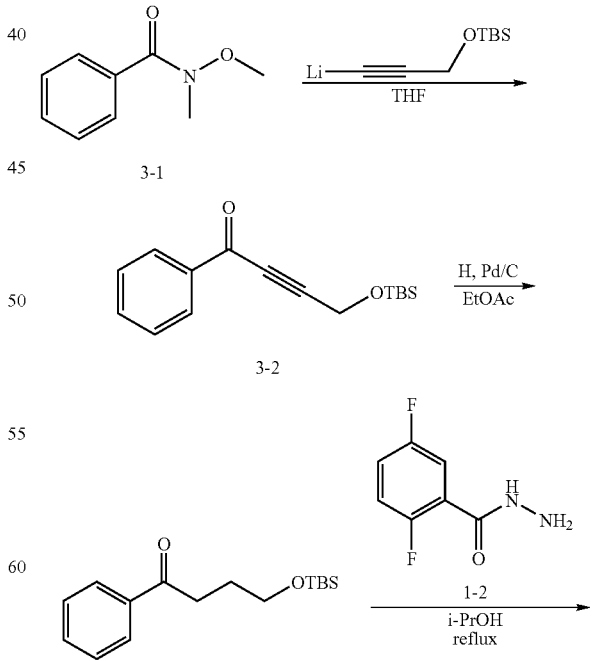

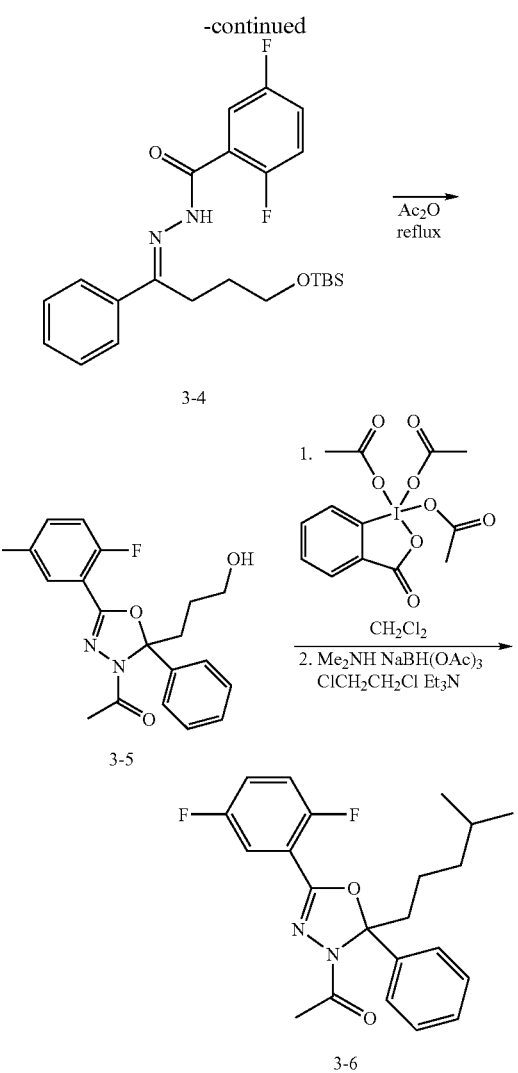

4-{[tert-butyl(dimethyl)silyl]oxy}-1-phenylbutan-1-one (3-3)

A mixture of 4-{[tert-butyl(dimethyl)silyl]oxy}-1-phenyl-but-2-yn-1-one (3-2, 6.60 g, 24.0 mmol, 1 equiv) and 10% Pd/C (4.0 g) in EtOAc (100 mL) was stirred under a hydrogen balloon for 75 minutes. The catalyst was filtered and washed with EtOAc (200 mL). The combined filtrate was concentrated and the residue purified by flash column chromatography (silica, 100% hexanes, grading to 50% EtOAc in hexanes) to provide 4-{[tert-butyl(dimethyl)silyl]oxy}-1-phenylbutan-1-one (3-3) as a light yellow oil. $^1$H NMR (300 MHz, CDCl$_3$) δ 7.97 (m, 2H), 7.55 (m, 1H), 7.46 (m, 2H), 3.71 (t, 2H, J=6.1 Hz), 3.07 (t, 2H, J=7.3 Hz), 1.96 (m, 2H), 0.89 (s, 9H), 0.05 (s, 6H).

3-[3-acetyl-5-(2,5-difluorophenyl)-2-phenyl-2,3-dihydro-1,3,4-oxadiazol-2-yl]propan-1-ol (3-5)

A solution of 2,5-difluorobenzohydrazide (1-2, 90 mg, 0.52 mmol, 1 equiv) and 4-{[tert-butyl(dimethyl)silyl]oxy}-1-phenylbutan-1-one (3-3) (146 mg, 0.523 mmol, 1.00 equiv) in isopropanol (10 mL) was heated at 75° C. for 1 day. The reaction mixture was concentrated to give N'-((1E)-4-{[tert-butyl(dimethyl)silyl]oxy}-1-phenylbutylidene)-2,5-difluorobenzohydrazide (3-4); LRMS m/z (M+H) 433.4 found, 433.2 required. A solution of 3-4 in acetic anhydride (5 mL) was heated at reflux for 1.5 h. The reaction mixture was concentrated and the residue was purified by reverse-phase LC(H$_2$O/CH$_3$CN gradient w/0.1% TFA present) to provide 3-[3-acetyl-5-(2,5-difluorophenyl)-2-phenyl-2,3-dihydro-1,3,4-oxadiazol-2-yl]propan-1-ol (3-5) as a colorless oil. $^1$H NMR (300 MHz, CDCl$_3$) δ 7.57 (m, 2H), 7.52 (m, 1H), 7.39 (m, 3H), 7.18 (m, 2H), 3.75 (t, 2H, J=6.4 Hz), 3.07 (m, 1H), 2.64 (m, 1H), 2.39 (s, 3H), 1.72 (m, 2H). LRMS m/z (M+H) 361.3 found, 361.1 required.

3-[3-acetyl-5-(2,5-difluorophenyl)-2-phenyl-2,3-dihydro-1,3,4-oxadiazol-2-yl]-N,N-dimethylpropan-1-amine (3-6)

3-[3-acetyl-5-(2,5-difluorophenyl)-2-phenyl-2,3-dihydro-1,3,4-oxadiazol-2-yl]propan-1-ol (3-5, 25 mg, 69 umol) was dissolved in anhydrous CH$_2$Cl$_2$ (1 mL) and was treated with Dess-Martin periodinane (50 mg, 118 umol) and the resulting cloudy yellow solution was stirred 1.5 h. Upon completion, the cloudy solution was treated with 1 mL sat. sodium thiosulfate/NaHCO$_3$ solution (1:1) and stirred 30 min. The mixture was extracted with EtOAc (3×5 mL), and the combined organics were dried (MgSO$_4$), filtered and concentrated. The crude residue 3-[3-acetyl-5-(2,5-difluorophenyl)-2-phenyl-2,3-dihydro-1,3,4-oxadiazol-2-yl]propanal was carried directly into the next transformation. 3-(2-Acetyl-8-chloro-3-phenyl-3a,4-dihydro-3H-pyrazolo[5,1-c][1,4]benzoxazin-3-yl)propanal (25 mg, 39 mmol) was dissolved in anhydrous dichloroethane (1 mL) and treated sequentially with dimethylamine (2.0 M in THF, 42 μL, 84 mmol), triethylamine (19 μL, 140 umol) and Na(OAc)$_3$BH (22 mg, 105 μmol). The reaction stirred 1 h at ambient temperature and was loaded directly onto a hexane flushed ISCO Redisep Column. Flash chromatography (Redisep® 12 g, 0-100% (3:1 EtOAc/(20:1:1 EtOH/NH$_4$OH/H$_2$O))/hexanes gradient) provided 3-[3-acetyl-5-(2,5-difluorophenyl)-2-phenyl-2,3-dihydro-1,3,4-oxadiazol-2-yl]-N,N-dimethylpropan-1-amine (3-6) as a clear oil. $^1$H NMR (300 MHz, CDCl$_3$) δ 7.58 (m, 2H), 7.51 (m, 1H), 7.37 (m, 3H), 7.16 (m, 2H), 2.91 (m, 1H), 2.54 (m, 1H), 2.36 (m, 2H), 2.35 (s, 3H), 2.21 (s, 6H), 1.61 (m, 2H); MS (M+H$^+$, C$_{21}$H$_{23}$F$_2$N$_3$O$_2$) 388.4 found 388.4 required.

4-{[tert-butyl(dimethyl)silyl]oxy}-1-phenylbut-2-yn-1-one (3-2)

A solution of n-BuLi in hexanes (1.6 M, 22.7 mL, 36.3 mmol, 1.20 equiv) was added to a solution of tert-butyl(dimethyl)(prop-2-yn-1-yloxy)silane (7.37 mL, 36.3 mmol, 1.20 equiv) in THF (150 mL) at −78° C. and the resultant mixture was stirred for 1 hour. N-methoxy-N-methylbenzamide (4.61 mL, 30.3 mmol, 1 equiv) was added and the reaction mixture was warmed to 23° C. and stirred for 16 h. The reaction mixture was partitioned between a 1:1 mixture of saturated ammonium chloride solution and brine (200 mL) and ethyl acetate (250 mL). The organic layer was dried over sodium sulfate and concentrated. The residue was purified by flash column chromatography (silica, 100% hexanes, grading to 50% EtOAc in hexanes) to provide 4-{[tert-butyl(dimethyl)silyl]oxy}-1-phenylbut-2-yn-1-one (3-2) as a light yellow oil. $^1$H NMR (300 MHz, CDCl$_3$) δ 8.15 (m, 2H), 7.62 (m, 1H), 7.48 (m, 2H), 4.60 (s, 2H), 0.95 (s, 9H), 0.18 (s, 6H).

Assays

The compounds of the instant invention described in the Examples were tested by the assays described below and were found to have kinase inhibitory activity. Other assays are known in the literature and could be readily performed by those of skill in the art (see, for example, PCT Publication WO 01/30768, May 3, 2001, pages 18-22).

I. Kinesin ATPase In Vitro Assay

Cloning and expression of human poly-histidine tagged KSP motor domain (KSP(367H)): Plasmids for the expression of the human KSP motor domain construct were cloned by PCR using a pBluescript full length human KSP construct (Blangy et al., Cell, vol. 83, pp 1159-1169, 1995) as a template.

The N-terminal primer
(SEQ.ID.NO.: 1)
5'-GCAACGATTAATATGGCGTCGCAGCCAAATTCGTCTGCGAAG
and the C-terminal primer
(SEQ.ID.NO.: 2)
5'-GCAACGCTCGAGTCAGTGATGATGGTGGTGATGCTGATTCACTTCAG
GCTTATTCAATAT were used to amplify the motor domain and the neck linker region. The PCR products were digested with AseI and XhoI, ligated into the NdeI/XhoI digestion product of pRSETa (Invitrogen) and transformed into E. coli BL21 (DE3).

Cells were grown at 37° C. to an $OD_{600}$ of 0.5. After cooling the culture to room temperature expression of KSP was induced with 100 µM IPTG and incubation was continued overnight. Cells were pelleted by centrifugation and washed once with ice-cold PBS. Pellets were flash-frozen and stored –80° C.

Protein Purification: Cell pellets were thawed on ice and resuspended in lysis buffer (50 mM K-HEPES, pH 8.0, 250 mM KCl, 0.1% Tween, 10 mM imidazole, 0.5 mM Mg-ATP, 1 mM PMSF, 2 mM benzimidine, 1× complete protease inhibitor cocktail (Roche)). Cell suspensions were incubated with 1 mg/ml lysozyme and 5 mM β-mercaptoethanol on ice for 10 minutes, followed by sonication (3×30 sec). All subsequent procedures were performed at 4° C. Lysates were centrifuged at 40,000×g for 40 minutes. Supernatants were diluted and loaded onto an SP Sepharose column (Pharmacia, 5 ml cartridge) in buffer A (50 mM K-HEPES, pH 6.8, 1 mM $MgCl_2$, 1 mM EGTA, 10 µM Mg-ATP, 1 mM DTT) and eluted with a 0 to 750 mM KCl gradient in buffer A. Fractions containing KSP were pooled and incubated with Ni-NTA resin (Qiagen) for one hour. The resin was washed three times with buffer B (Lysis buffer minus PMSF and protease inhibitor cocktail), followed by three 15-minute incubations and washes with buffer B. Finally, the resin was incubated and washed for 15 minutes three times with buffer C (same as buffer B except for pH 6.0) and poured into a column. KSP was eluted with elution buffer (identical to buffer B except for 150 mM KCl and 250 mM imidazole). KSP-containing fractions were pooled, made 10% in sucrose, and stored at –80° C.

Microtubules are prepared from tubulin isolated from bovine brain. Purified tubulin (>97% MAP-free) at 1 mg/ml is polymerized at 37° C. in the presence of 10 µM paclitaxel, 1 mM DTT, 1 mM GTP in BRB80 buffer (80 mM K-PIPES, 1 mM EGTA, 1 mM $MgCl_2$ at pH 6.8). The resulting microtubules are separated from non-polymerized tubulin by ultracentrifugation and removal of the supernatant. The pellet, containing the microtubules, is gently resuspended in 10 µM paclitaxel, 1 mM DTT, 50 µg/ml ampicillin, and 5 µg/ml chloramphenicol in BRB80.

The kinesin motor domain is incubated with microtubules, 1 mM ATP (1:1 $MgCl_2$: Na-ATP), and compound at 23° C. in buffer containing 80 mM K-HEPES (pH 7.0), 1 mM EGTA, 1 mM DTT, 1 mM $MgCl_2$, and 50 mM KCl. The reaction is terminated by a 2-10 fold dilution with a final buffer composition of 80 mM HEPES and 50 mM EDTA. Free phosphate from the ATP hydrolysis reaction is measured via a quinaldine red/ammonium molybdate assay by adding 150 µl of quench C buffer containing a 2:1 ratio of quench A:quench B. Quench A contains 0.1 mg/ml quinaldine red and 0.14% polyvinyl alcohol; quench B contains 12.3 mM ammonium molybdate tetrahydrate in 1.15 M sulfuric acid. The reaction is incubated for 10 minutes at 23° C., and the absorbance of the phospho-molybdate complex is measured at 540 nm.

The compounds shown in the Examples were tested in the above assay and found to have an $IC_{50} \leq 30$ µM.

II. Cell Proliferation Assay

Cells are plated in 96-well tissue culture dishes at densities that allow for logarithmic growth over the course of 24, 48, and 72 hours and allowed to adhere overnight. The following day, compounds are added in a 10-point, one-half log titration to all plates. Each titration series is performed in triplicate, and a constant DMSO concentration of 0.1% is maintained throughout the assay. Controls of 0.1% DMSO alone are also included. Each compound dilution series is made in media without serum. The final concentration of serum in the assay is 5% in a 200 µL volume of media. Twenty microliters of Alamar blue staining reagent is added to each sample and control well on the titration plate at 24, 48, or 72 hours following the addition of drug and returned to incubation at 37° C. Alamar blue fluorescence is analyzed 6-12 hours later on a CytoFluor II plate reader using 530-560 nanometer wavelength excitation, 590 nanometer emission.

A cytotoxic $EC_{50}$ is derived by plotting compound concentration on the x-axis and average percent inhibition of cell growth for each titration point on the y-axis. Growth of cells in control wells that have been treated with vehicle alone is defined as 100% growth for the assay, and the growth of cells treated with compounds is compared to this value. Proprietary in-house software is used to calculate percent cytotoxicity values and inflection points using logistic 4-parameter curve fitting. Percent cytotoxicity is defined as:

$$\% \text{ cytotoxicity:} (\text{Fluorescence}_{control} - \text{Flourescence}_{sample}) \times 100 \times (\text{Fluorescence}_{control})^{-1}$$

The inflection point is reported as the cytotoxic $EC_{50}$.

III. Evaluation of Mitotic Arrest and Apoptosis by FACS

FACS analysis is used to evaluate the ability of a compound to arrest cells in mitosis and to induce apoptosis by measuring DNA content in a treated population of cells. Cells are seeded at a density of $1.4 \times 10^6$ cells per 6 $cm^2$ tissue culture dish and allowed to adhere overnight. Cells are then treated with vehicle (0.1% DMSO) or a titration series of compound for 8-16 hours. Following treatment, cells are harvested by trypsinization at the indicated times and pelleted by centrifugation. Cell pellets are rinsed in PBS and fixed in 70% ethanol and stored at 4° C. overnight or longer.

For FACS analysis, at least 500,000 fixed cells are pelleted and the 70% ethanol is removed by aspiration. Cells are then incubated for 30 min at 4° C. with RNase A (50 Kunitz units/ml) and propidium iodide (50 μg/ml), and analyzed using a Becton Dickinson FACSCaliber. Data (from 10,000 cells) is analyzed using the Modfit cell cycle analysis modeling software (Verity Inc.).

blocking. Slides are incubated in primary antibodies (mouse monoclonal anti-α-tubulin antibody, clone DM1A from Sigma diluted 1:500; rabbit polyclonal anti-pericentrin antibody from Covance, diluted 1:2000) overnight at 4° C. After washing, slides are incubated with conjugated secondary antibodies (FITC-conjugated donkey anti-mouse IgG for tubulin; Texas red-conjugated donkey anti-rabbit IgG for pericentrin) diluted to 15 μg/ml for one hour at room temperature. Slides are then washed and counterstained with Hoechst 33342 to visualize DNA. Immunostained samples are imaged with a 100× oil immersion objective on a Nikon epifluorescence microscope using Metamorph deconvolution and imaging software.

```
                         SEQUENCE LISTING

<160> NUMBER OF SEQ ID NOS: 2

<210> SEQ ID NO 1
<211> LENGTH: 42
<212> TYPE: DNA
<213> ORGANISM: Artificial Sequence
<220> FEATURE:
<223> OTHER INFORMATION: Completely Synthetic Nucleotide Sequence

<400> SEQUENCE: 1
gcaacgatta atatggcgtc gcagccaaat tcgtctgcga ag                    42

<210> SEQ ID NO 2
<211> LENGTH: 60
<212> TYPE: DNA
<213> ORGANISM: Artificial Sequence
<220> FEATURE:
<223> OTHER INFORMATION: Completely Synthetic Nucleotide Sequence

<400> SEQUENCE: 2
gcaacgctcg agtcagtgat gatggtggtg atgctgattc acttcaggct tattcaatat    60
```

An $EC_{50}$ for mitotic arrest is derived by plotting compound concentration on the x-axis and percentage of cells in the G2/M phase of the cell cycle for each titration point (as measured by propidium iodide fluorescence) on the y-axis. Data analysis is performed using the SigmaPlot program to calculate an inflection point using logistic 4-parameter curve fitting. The inflection point is reported as the $EC_{50}$ for mitotic arrest. A similar method is used to determine the compound $EC_{50}$ for apoptosis. Here, the percentage of apoptotic cells at each titration point (as determined by propidium iodide fluorescence) is plotted on the y-axis, and a similar analysis is carried out as described above.

IV. Immunofluorescence Microscopy to Detect Monopolar Spindles

Methods for immunofluorescence staining of DNA, tubulin, and pericentrin are essentially as described in Kapoor et al. (2000) *J. Cell Biol.* 150: 975-988. For cell culture studies, cells are plated on tissue culture treated glass chamber slides and allowed to adhere overnight. Cells are then incubated with the compound of interest for 4 to 16 hours. After incubation is complete, media and drug are aspirated and the chamber and gasket are removed from the glass slide. Cells are then permeabilized, fixed, washed, and blocked for non-specific antibody binding according to the referenced protocol. Paraffin-embedded tumor sections are deparaffinized with xylene and rehydrated through an ethanol series prior to

What is claimed is:

1. The compound of the Formula III:

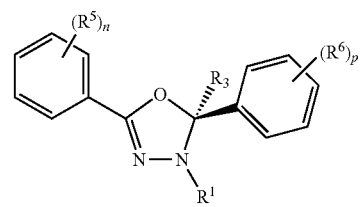

III wherein:

n and p are independently 0, 1, 2, 3, 4 or 5;

$R^1$ is (C=O)($C_1$-$C_6$)alkyl;

$R^3$ is selected from: H, ($C_1$-$C_6$)alkyl and ($C_1$-$C_6$)alkyl-N($R^d$)$_2$;

$R^5$ is halogen;

$R^6$ is independently selected from: H, ($C_1$-$C_6$)alkyl, halogen and OH;

$R^d$ is independently selected from: H and ($C_1$-$C_6$)alkyl;

or a pharmaceutically acceptable salt or stereoisomer thereof.

2. A pharmaceutical composition comprising a pharmaceutical carrier, and dispersed therein, a therapeutically effective amount of a compound of claim 1.

3. The compound of claim 1 which is selected from:
3-acetyl-5-(2,5-difluorophenyl)-2-phenyl-2,3-dihydro-1,3,4-oxadiazole;
3-acetyl-5-(2,5-difluorophenyl)-2-methyl-2-phenyl-2,3-dihydro-1,3,4-oxadiazole;
3-[3-acetyl-5-(2,5-difluorophenyl)-2-phenyl-2,3-dihydro-1,3,4-oxadiazol-2-yl]propan-1-ol; and
3-[3-acetyl-5-(2,5-difluorophenyl)-2-phenyl-2,3-dihydro-1,3,4-oxadiazol-2-yl]-N,N-dimethylpropan-1-amine;
or a pharmaceutically acceptable salt or stereoisomer thereof.

* * * * *